(12) United States Patent
Veenhof et al.

(10) Patent No.: US 11,571,204 B2
(45) Date of Patent: Feb. 7, 2023

(54) SUTURE DEVICE

(71) Applicant: MEDICLOSE SOLUTIONS B.V., Maastricht (NL)

(72) Inventors: Alexander Arnold Frederik Adriaan Veenhof, Maastricht (NL); Micha Ilan Paalman, Maastricht (NL)

(73) Assignee: MEDICLOSE SOLUTIONS B.V., Maastricht (NL)

( * ) Notice: Subject to any disclaimer, the term of this patent is extended or adjusted under 35 U.S.C. 154(b) by 326 days.

(21) Appl. No.: 16/766,474

(22) PCT Filed: Nov. 26, 2018

(86) PCT No.: PCT/NL2018/050793
§ 371 (c)(1),
(2) Date: May 22, 2020

(87) PCT Pub. No.: WO2019/103615
PCT Pub. Date: May 31, 2019

(65) Prior Publication Data
US 2020/0375588 A1 Dec. 3, 2020

(30) Foreign Application Priority Data
Nov. 24, 2017 (NL) ..................................... 2019974

(51) Int. Cl.
*A61B 17/04* (2006.01)
*A61B 17/06* (2006.01)
(52) U.S. Cl.
CPC .... *A61B 17/0469* (2013.01); *A61B 17/06061* (2013.01); *A61B 2017/047* (2013.01); *A61B 2017/0472* (2013.01)
(58) Field of Classification Search
CPC .......... A61B 17/0469; A61B 17/06061; A61B 2017/047; A61B 2017/0472;
(Continued)

(56) References Cited

U.S. PATENT DOCUMENTS 5,586,986 A 12/1996 Hinchliffe
5,591,180 A 1/1997 Hinchliffe
(Continued)

FOREIGN PATENT DOCUMENTS

EP 0830843 A1 3/1998
EP 2308378 A2 4/2011
(Continued)

OTHER PUBLICATIONS

International Search Report dated May 14, 2019, for corresponding international Patent Application No. PCT/NL2018/050793, filed Nov. 26, 2018.
(Continued)

*Primary Examiner* — Julian W Woo
(74) *Attorney, Agent, or Firm* — Steven M. Koehler; Westman, Champlin & Koehler, P.A.

(57) ABSTRACT

A suture device is provided comprising an elongate body having a longitudinal axis and opposite proximal and distal ends. The distal end inserts into a wound and the proximal end operates the device. A suture needle connects with the elongate body at or near the distal end and is movable relative to the elongate body in longitudinal direction along a needle trajectory having a suturing space. A spreader connects with the elongate body at or near the distal end and engages tissue to be sutured adjacent the needle trajectory and provides a pulling force on the tissue to pull a portion of the tissue into the suturing space; and/or comprises a spring. The device is configured to urge at least a portion of the suture needle from a first position to a second position along a needle trajectory past a suturing space by a spring action of the spring.

19 Claims, 13 Drawing Sheets

(58) Field of Classification Search
CPC ...... A61B 17/0057; A61B 2017/00637; A61B 2017/00663; A61B 2017/081; A61B 17/0482
See application file for complete search history.

(56) References Cited

U.S. PATENT DOCUMENTS

| | | | |
|---|---|---|---|
| 5,836,955 | A | 11/1998 | Buelna et al. |
| 5,846,253 | A | 12/1998 | Buelna et al. |
| 5,860,992 | A | 1/1999 | Daniel et al. |
| 6,551,330 | B1 | 4/2003 | Bain et al. |
| 7,544,199 | B2 | 6/2009 | Bain et al. |
| 8,771,296 | B2* | 7/2014 | Nobles ............... A61B 17/0469 606/144 |
| 9,649,106 | B2 | 5/2017 | Nobles et al. |
| 10,058,324 | B2 | 8/2018 | Van Loenen et al. |
| 10,610,216 | B2 | 4/2020 | Nobles et al. |
| 10,624,629 | B2* | 4/2020 | Nobles ............. A61B 17/06066 |
| 2003/0181925 | A1 | 9/2003 | Bain et al. |
| 2006/0259046 | A1 | 11/2006 | de la Torre et al. |
| 2007/0203507 | A1 | 8/2007 | McLaughlin et al. |
| 2008/0097481 | A1 | 4/2008 | Schorr et al. |
| 2010/0137888 | A1 | 6/2010 | Wulc et al. |
| 2011/0082473 | A1 | 4/2011 | Smith |
| 2011/0190793 | A1 | 8/2011 | Nobles et al. |
| 2014/0148825 | A1 | 5/2014 | Nobles et al. |
| 2014/0316442 | A1 | 10/2014 | Van Loenen et al. |
| 2017/0245853 | A1 | 8/2017 | Nobles et al. |
| 2017/0296168 | A1 | 10/2017 | Nobles et al. |

FOREIGN PATENT DOCUMENTS

| | | |
|---|---|---|
| WO | 0224078 A1 | 3/2002 |
| WO | 2007025302 A2 | 3/2007 |
| WO | 2011094619 A1 | 8/2011 |
| WO | 2012142338 A2 | 10/2012 |
| WO | 2013095090 A2 | 6/2013 |

OTHER PUBLICATIONS

Written Opinion of the International Searching Authority dated May 14, 2019, for corresponding International Patent Application No. PCT/NL2018/050793, filed Nov. 26, 2018.

* cited by examiner

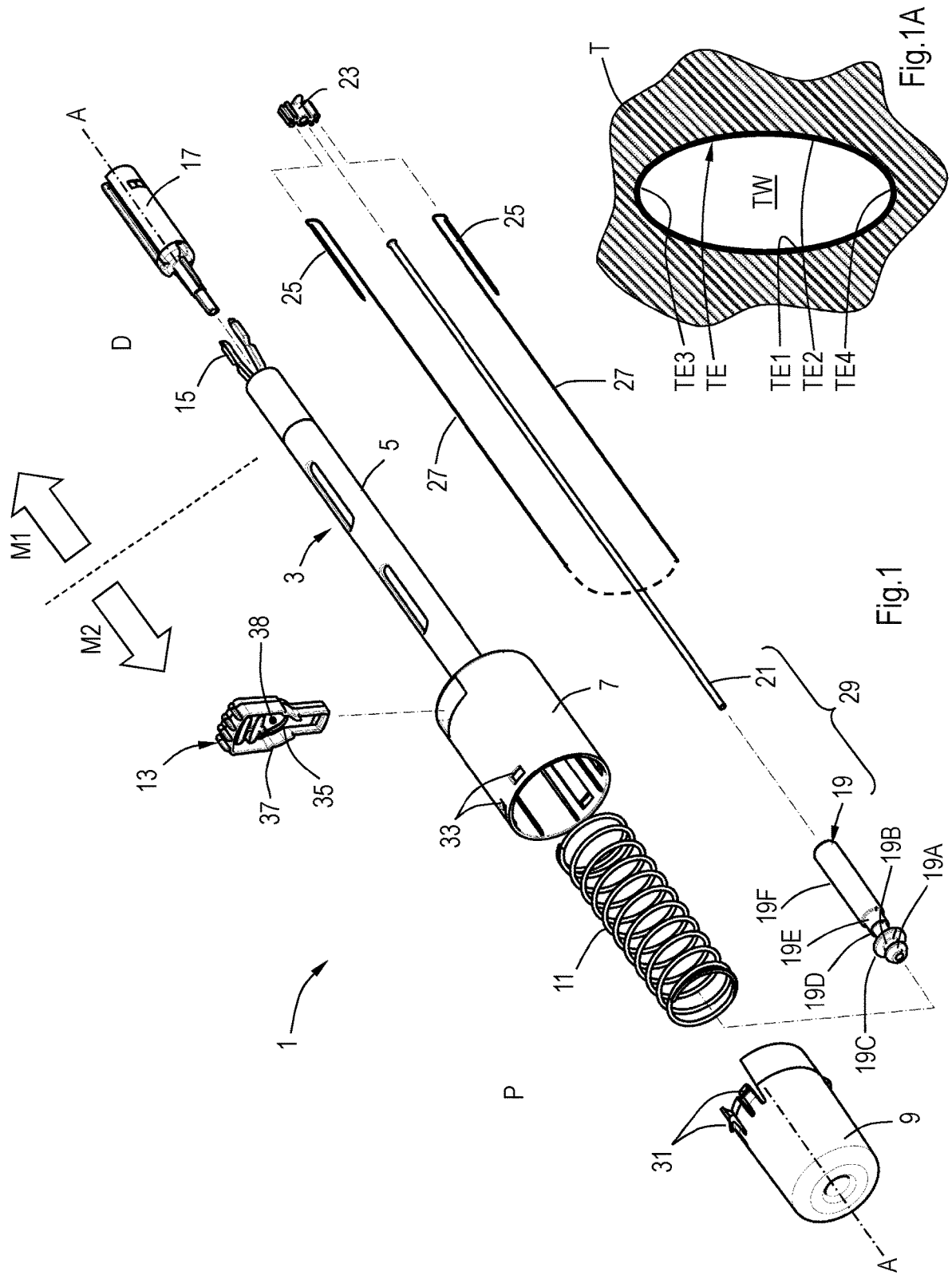

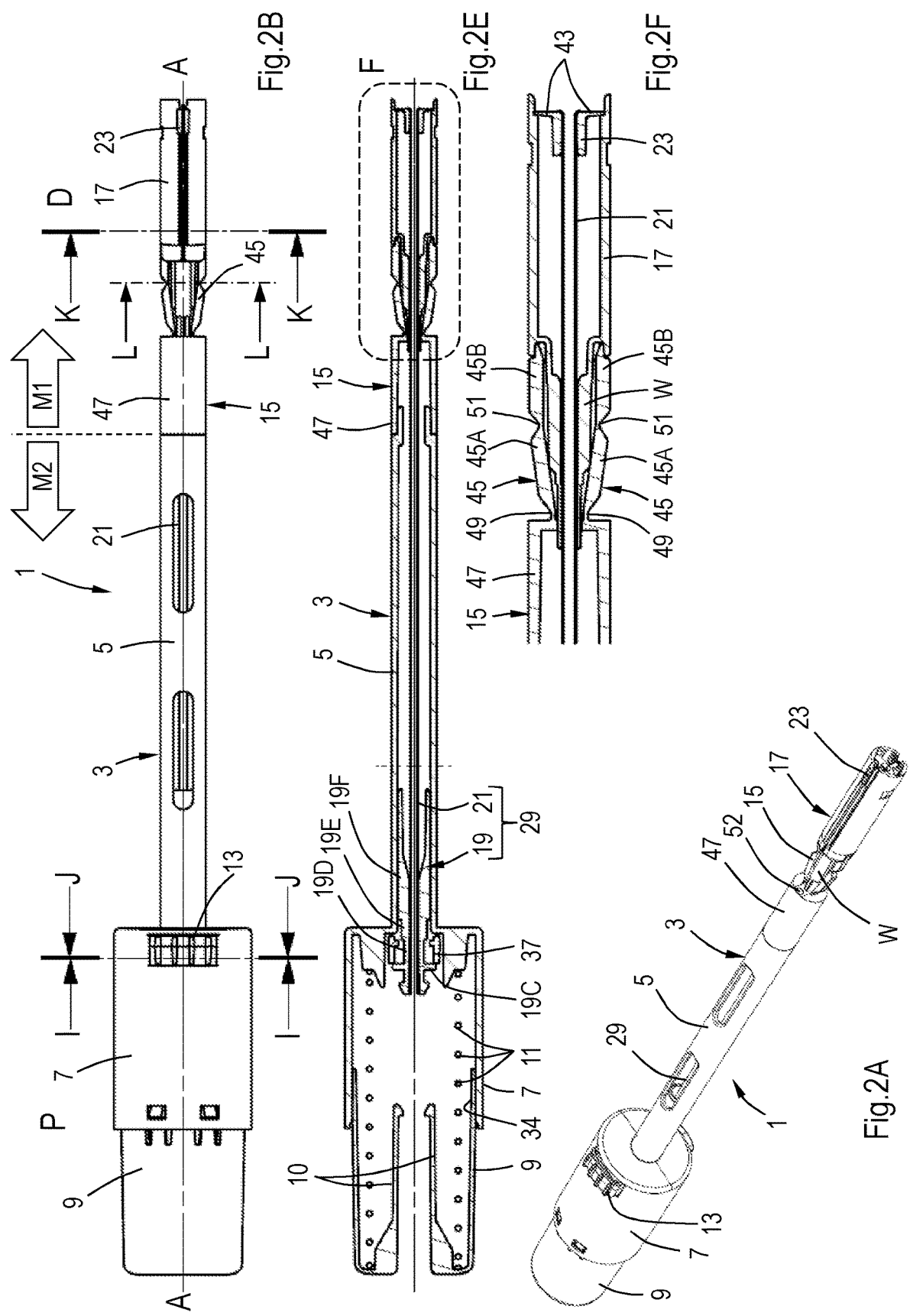

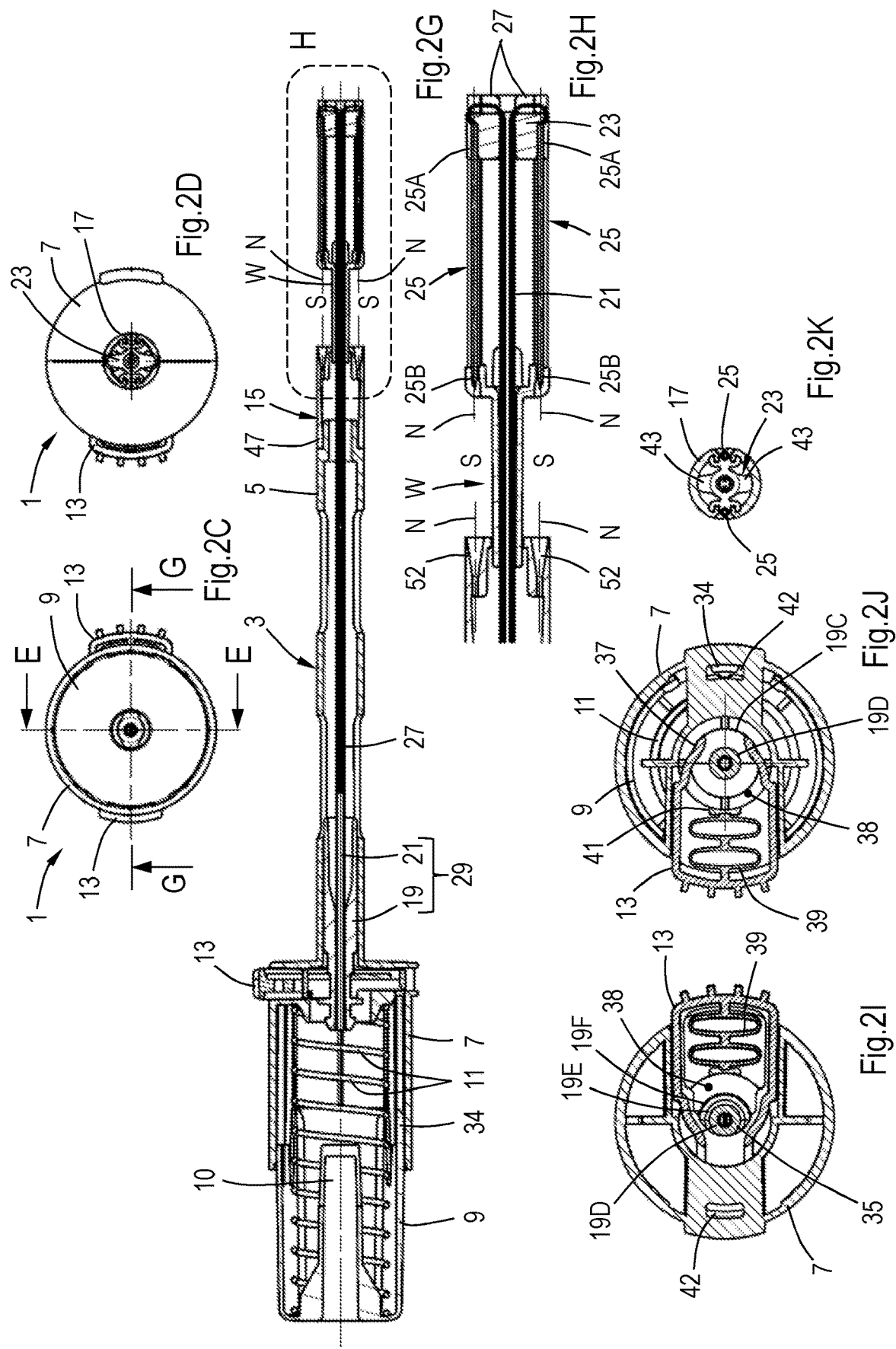

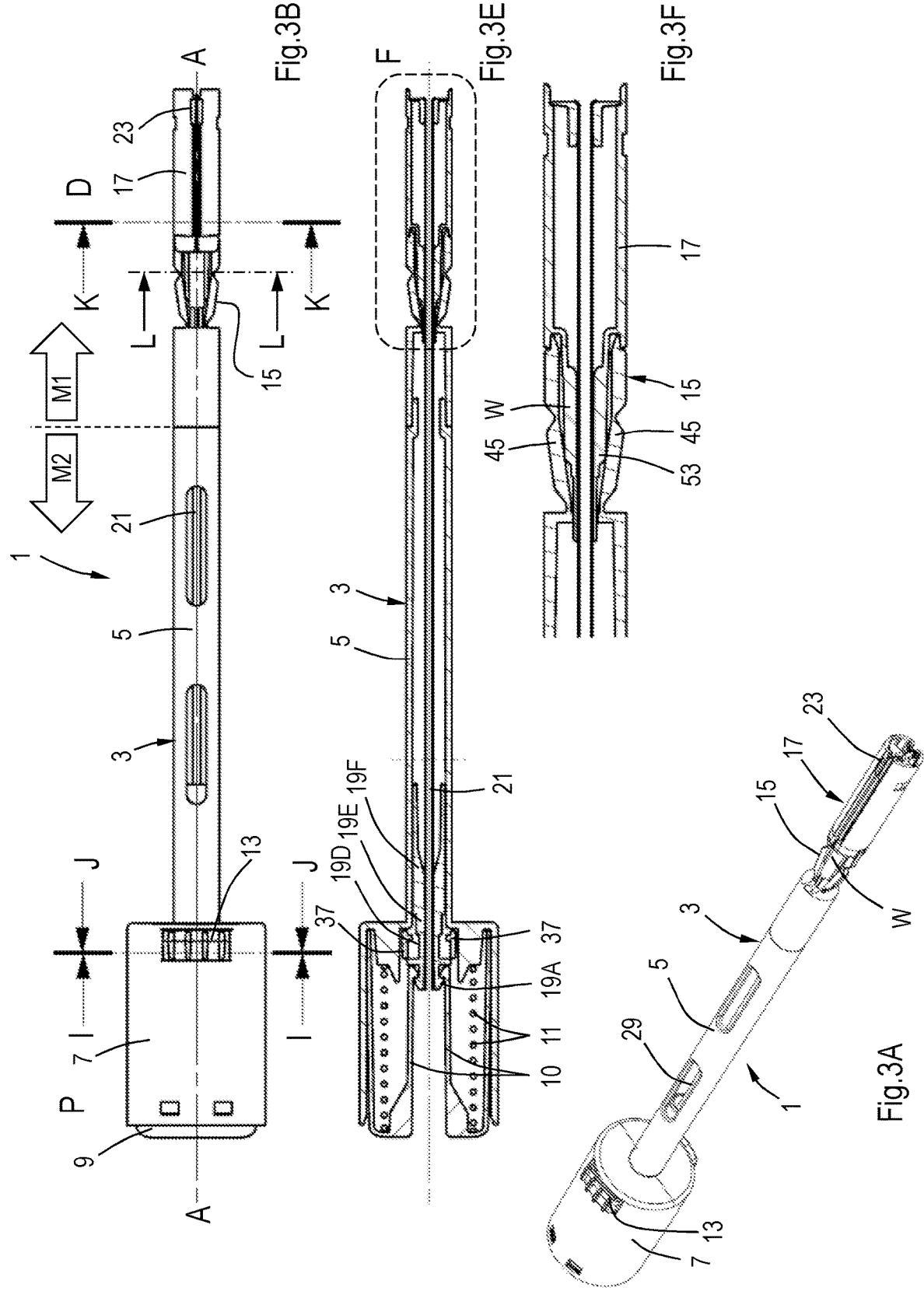

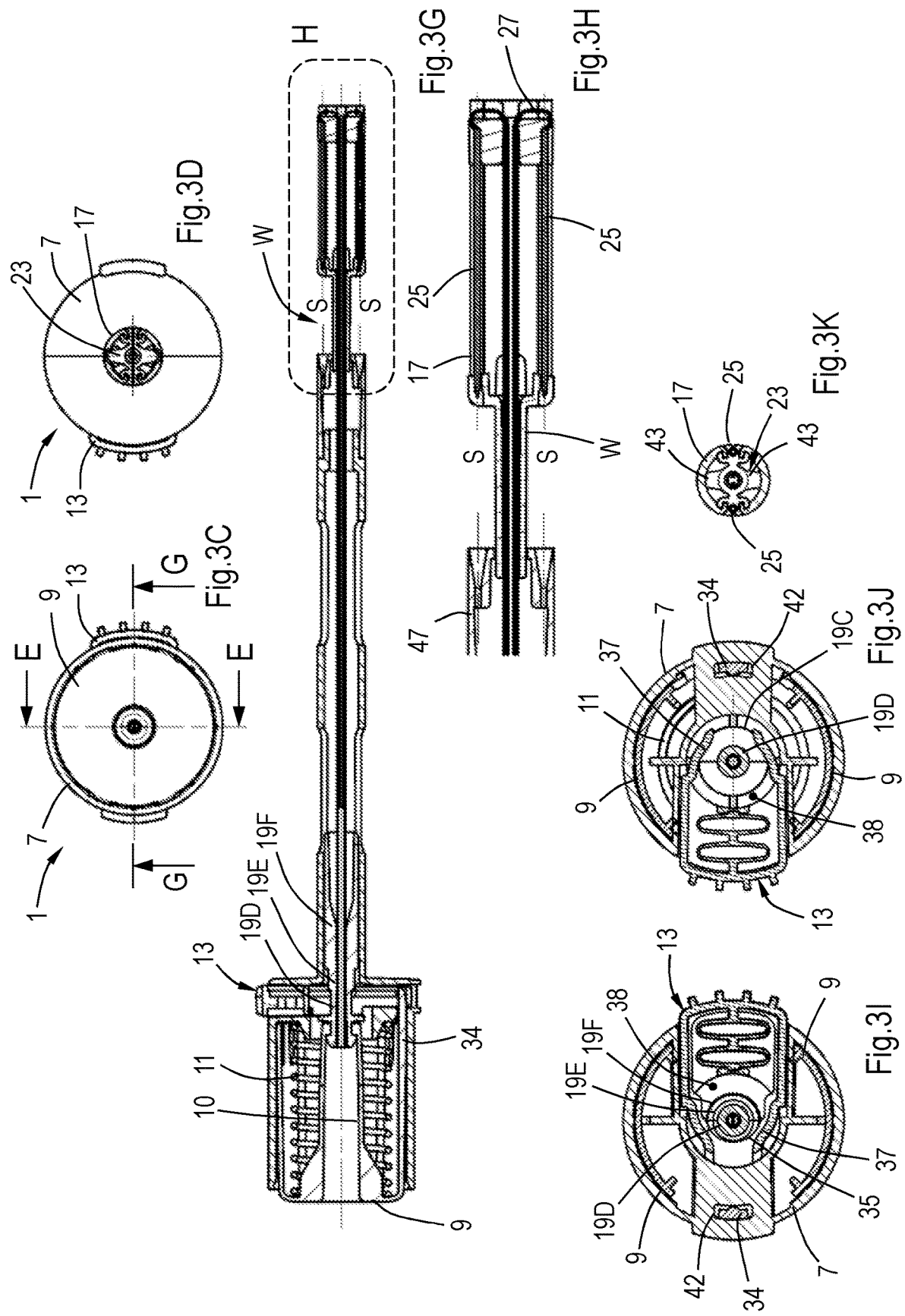

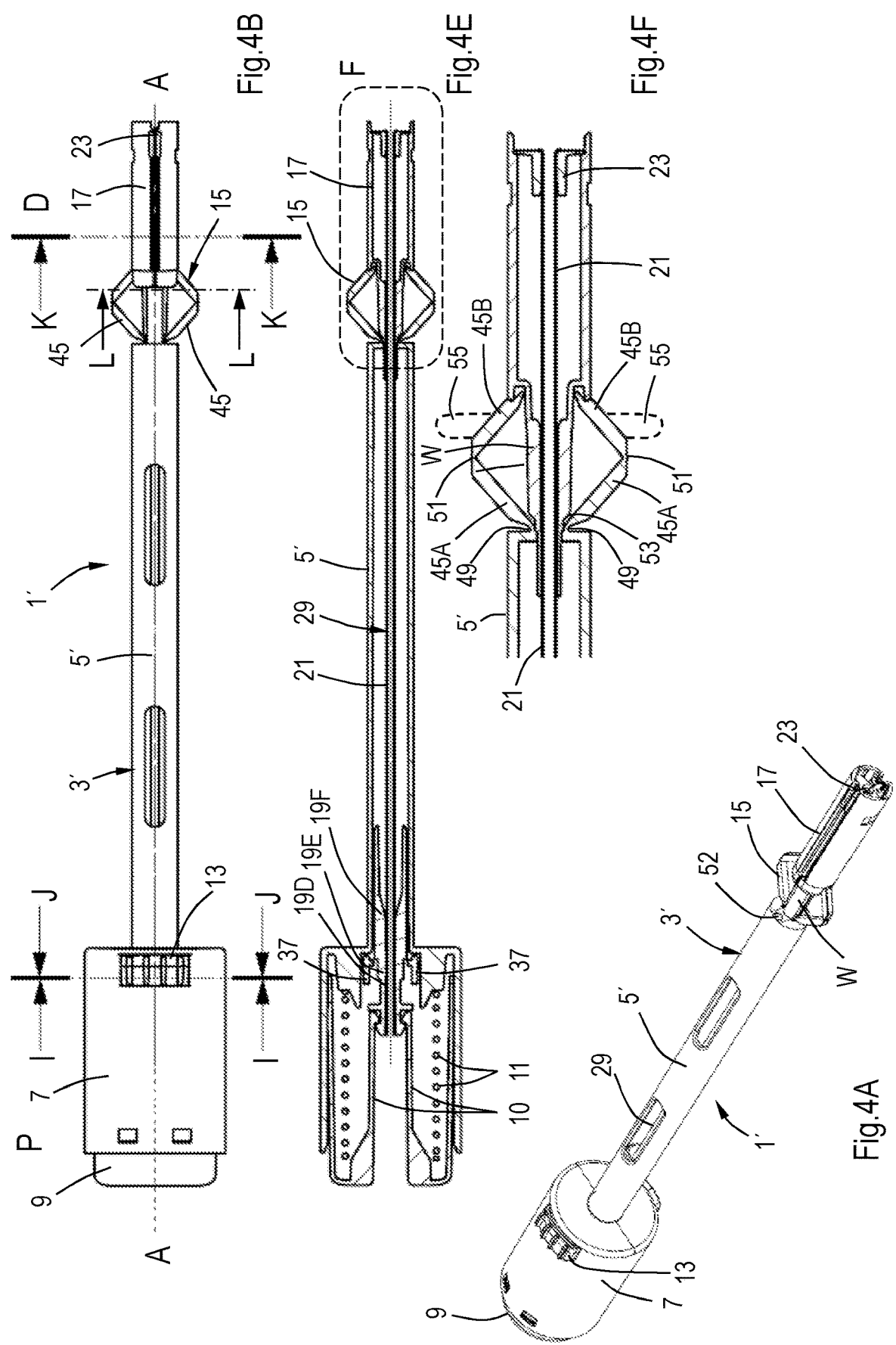

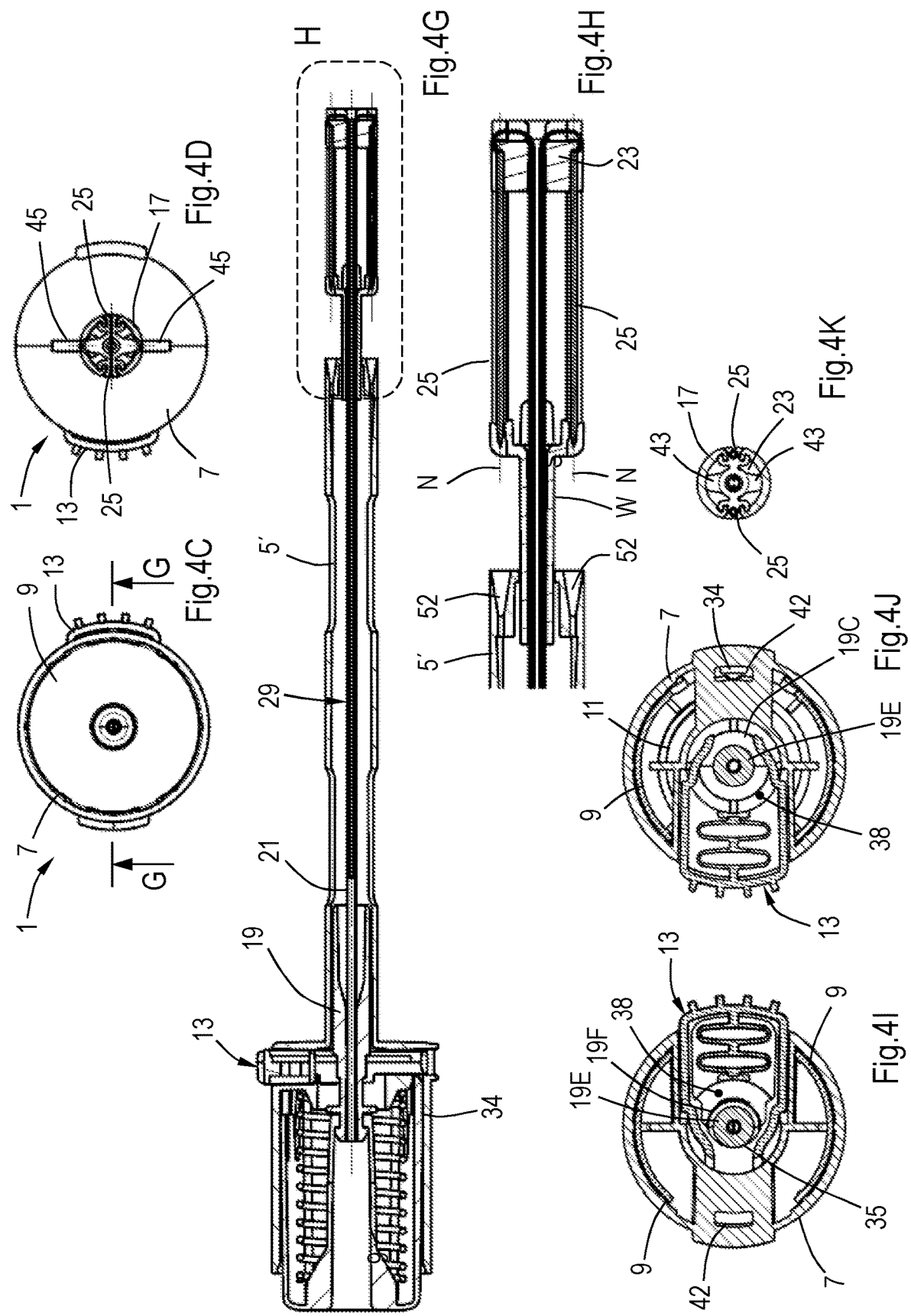

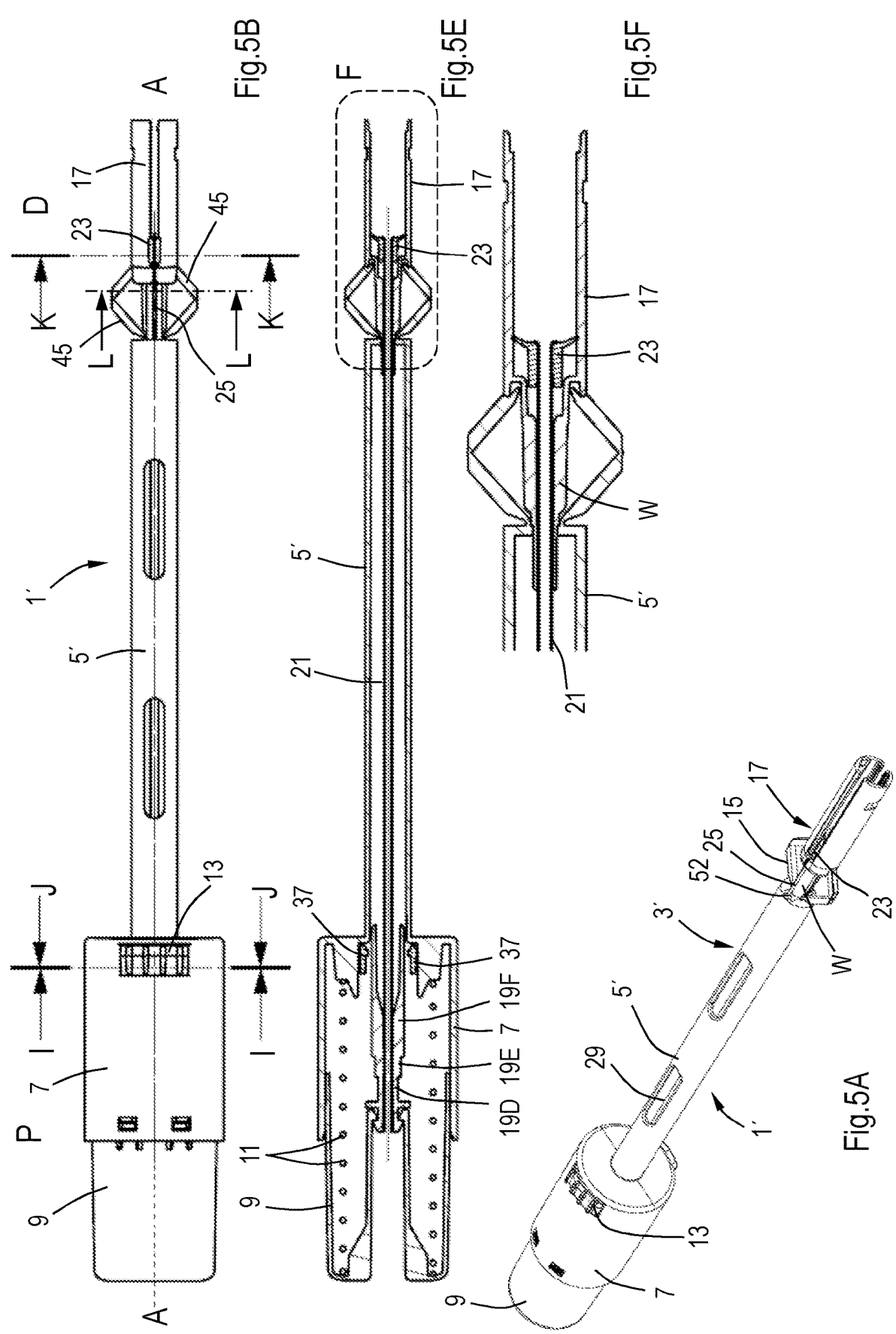

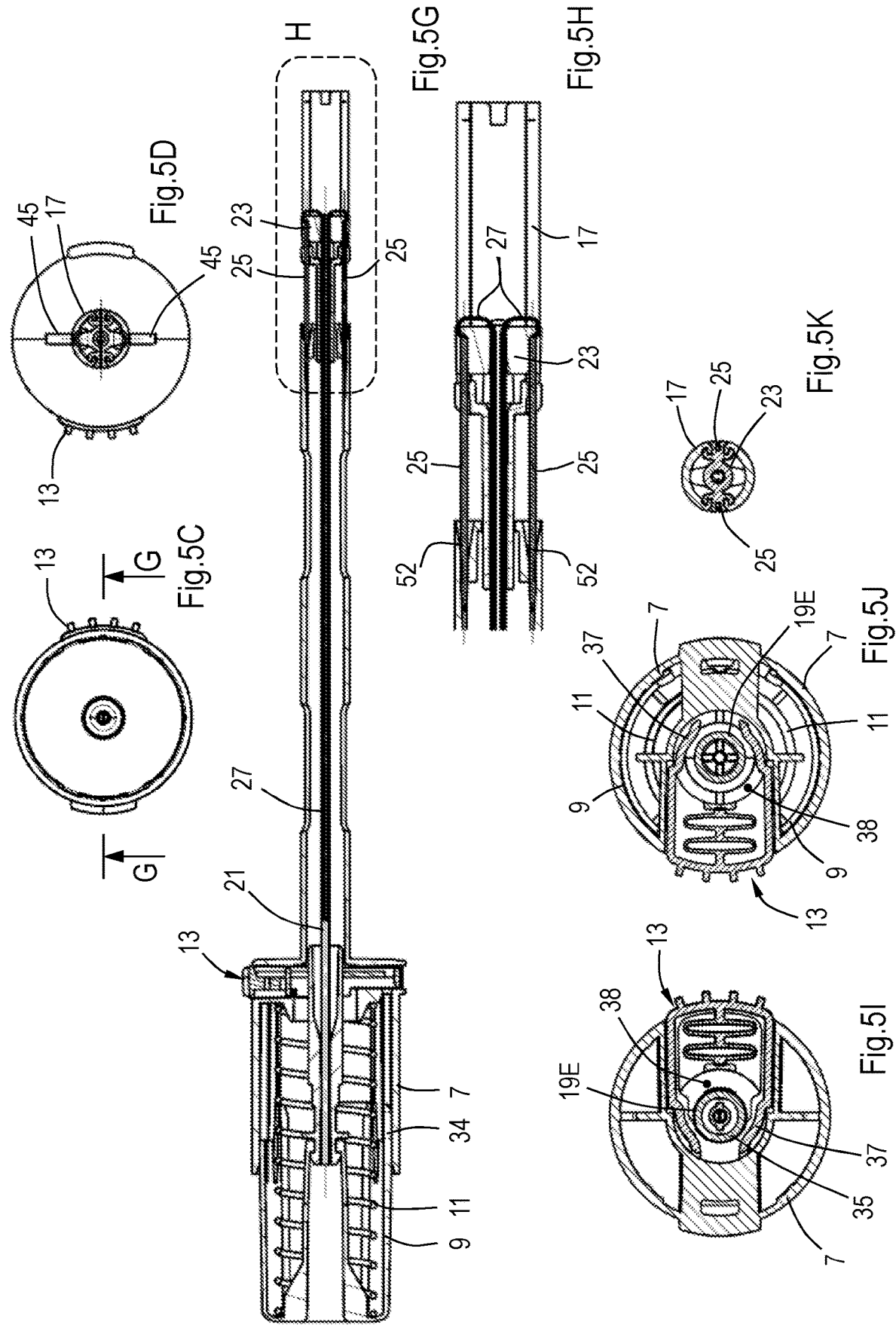

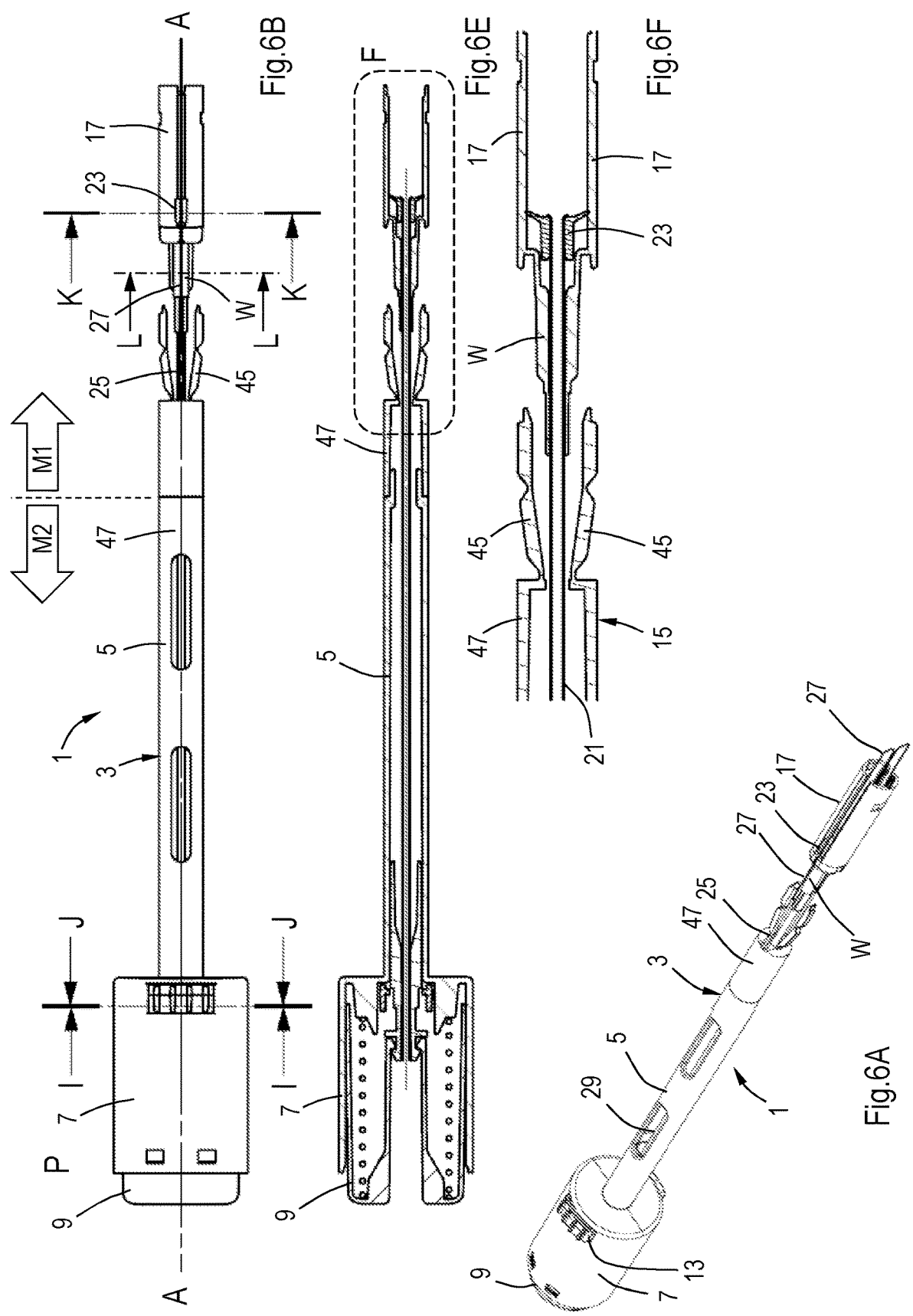

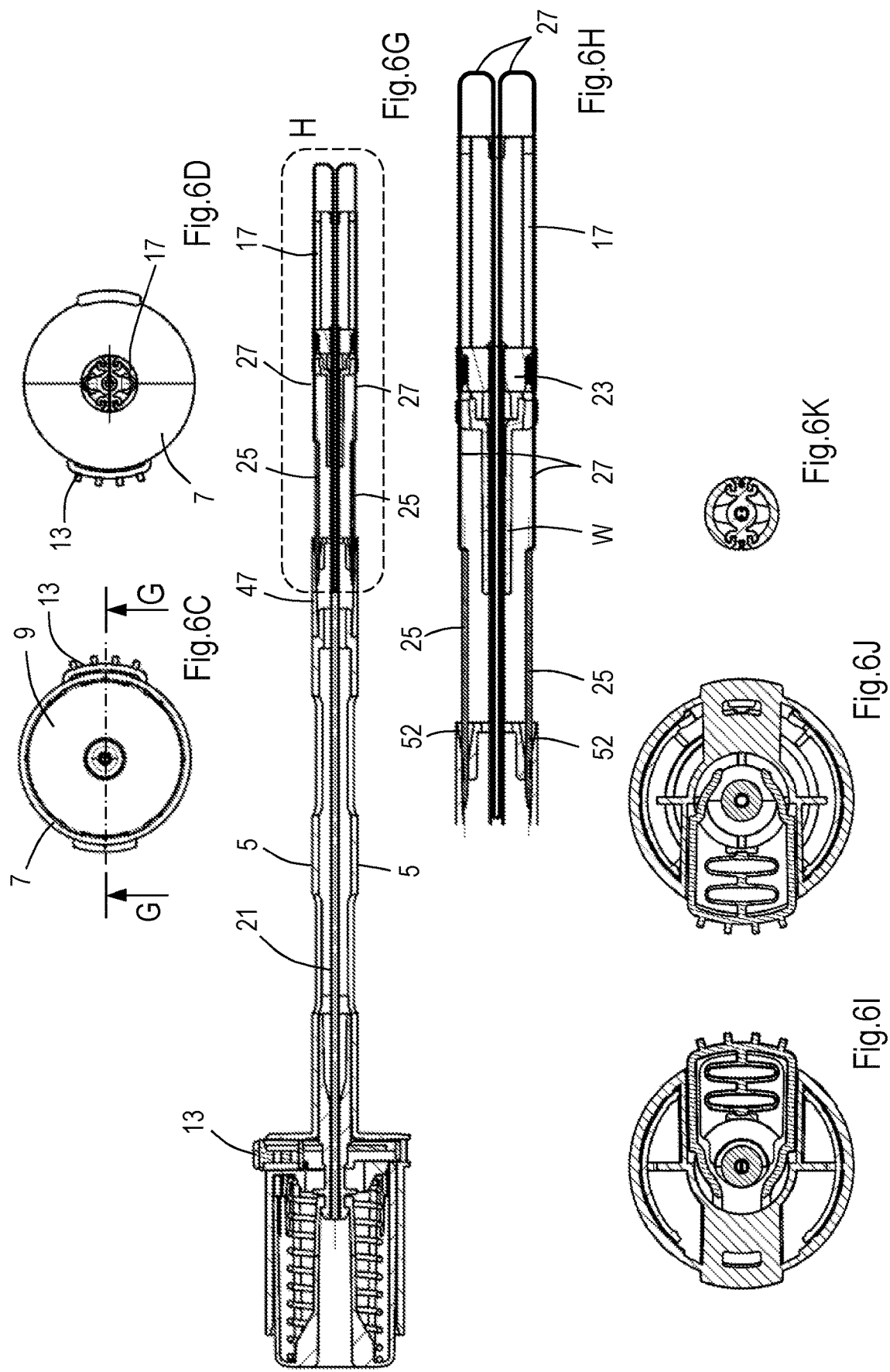

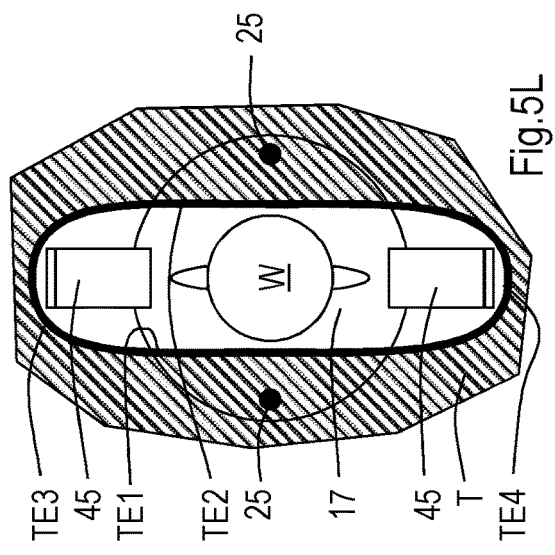
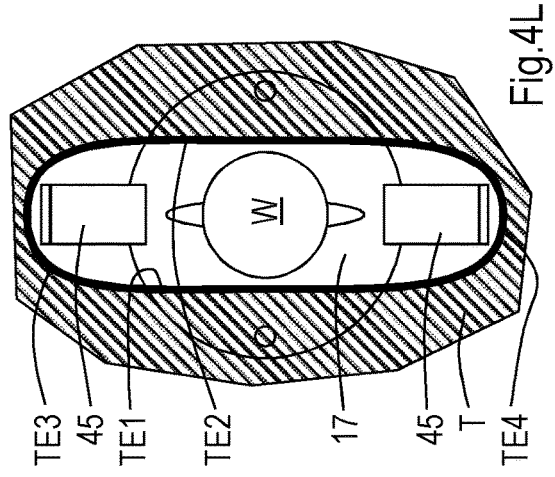
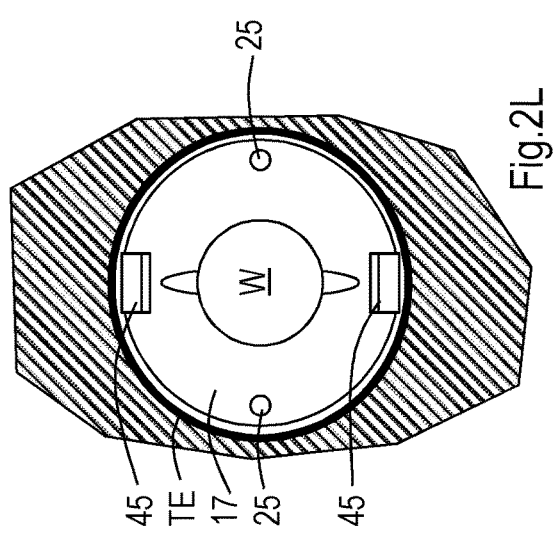
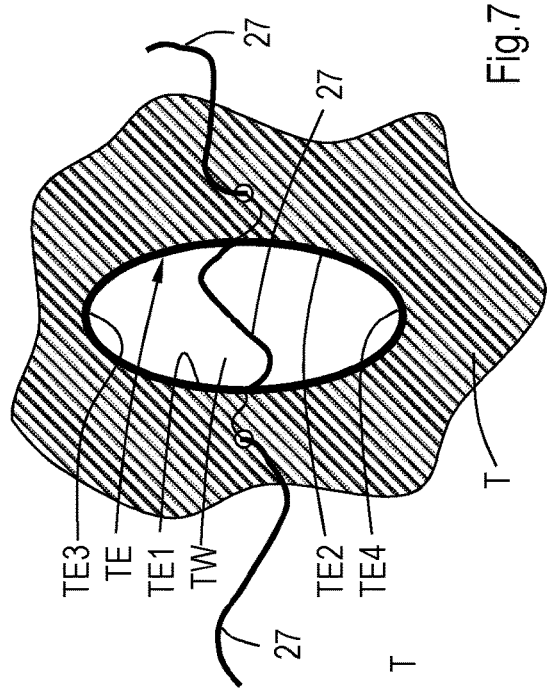
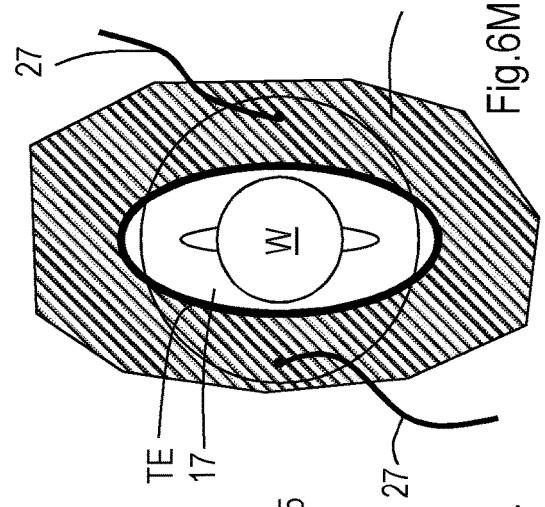
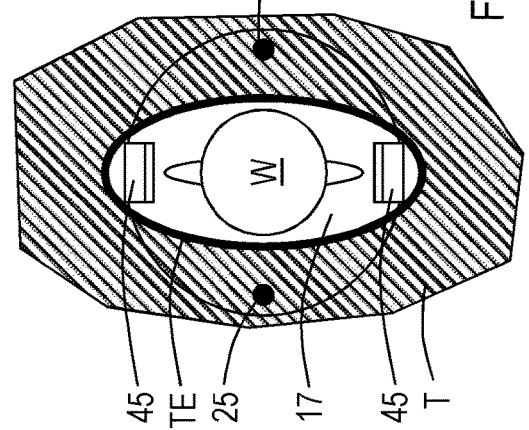

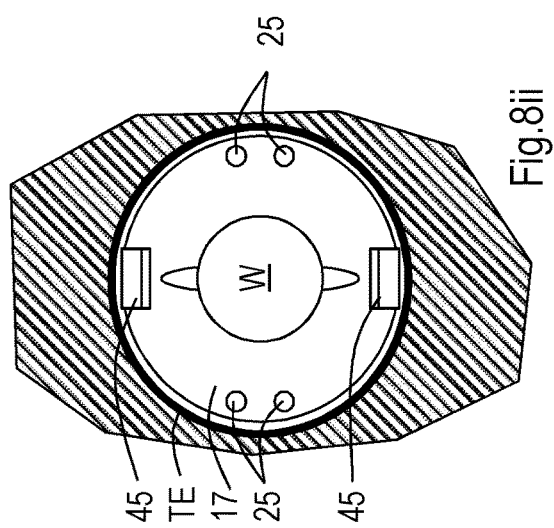
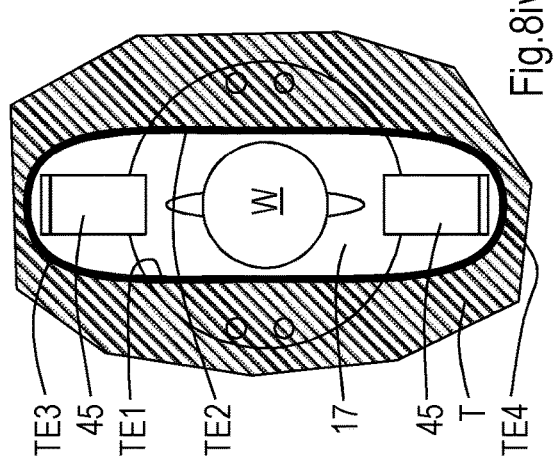
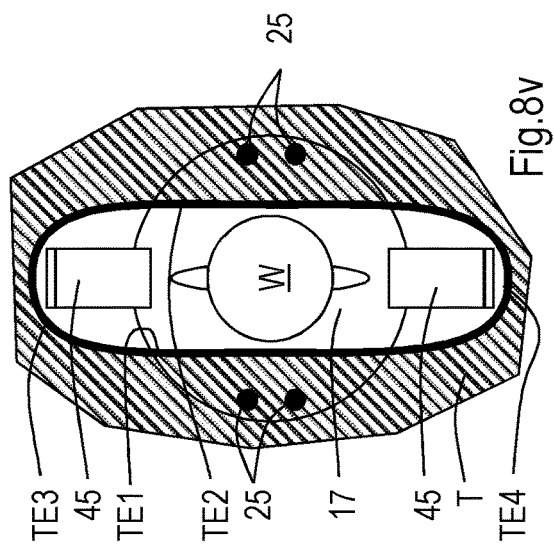
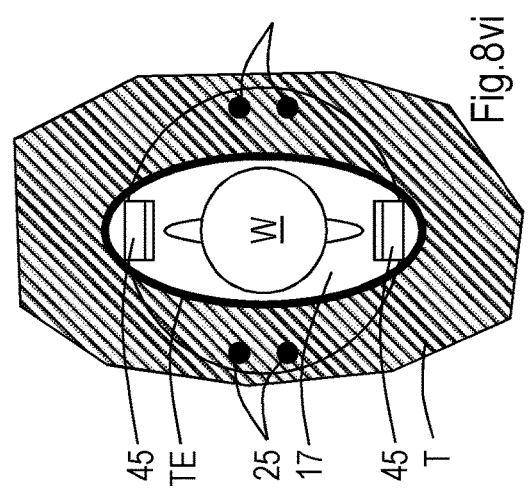
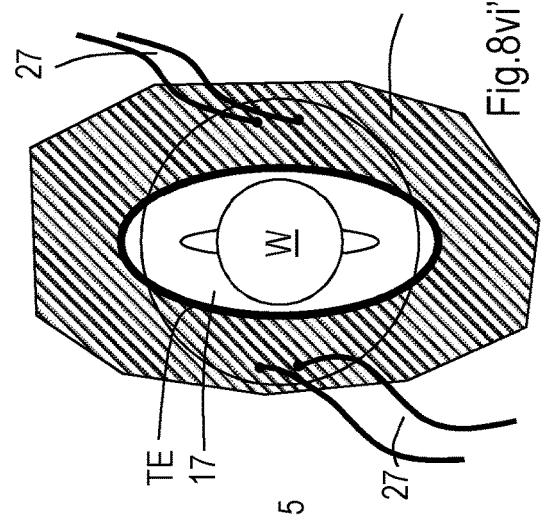
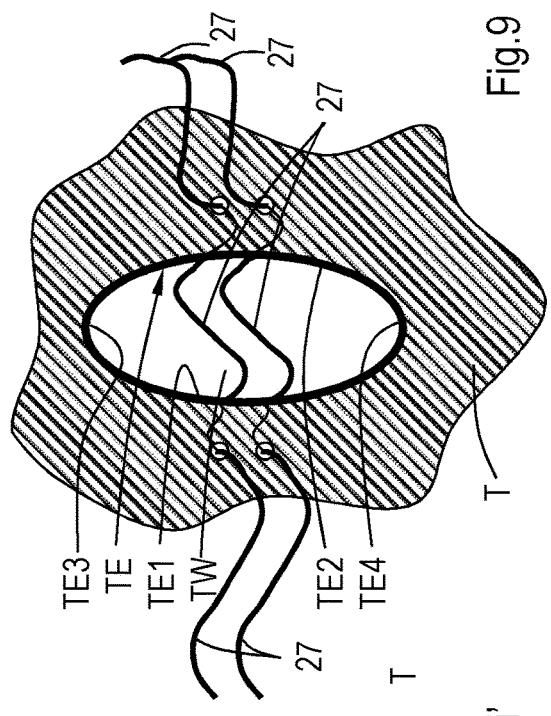

SUTURE DEVICE

CROSS-REFERENCE TO RELATED APPLICATION

The present application is a national stage of International patent application Serial No. PCT/NL2018/050793, filed Nov. 26, 2018, and published in English as WO 2019/103615.

TECHNICAL FIELD

The present disclosure relates to a suture device. More particularly, the invention relates to a suture device to suture tissue wounds, in particular trocar puncture wounds or similar.

BACKGROUND

With laparoscopic and endoscopic surgery, a small incision or puncture is made in the patient's body to provide access for a tube or a cannula device. A trocar may be provided to make this incision or puncture, and to form a cannula through the incision or puncture. Once extended into the patient's body, the trocar allows for insertion of various surgical instruments such as scissors, dissectors, retractors, or biopsy instruments to perform diagnostics and/or surgery.

Upon completion of the surgical procedure, the remaining puncture wound may require some attention, e.g., in the form of placing sutures to close the wound.

A suture device addressing one or more concerns and/or other desires, possibly representing conflicting interests, such as a device enabling placing sutures relatively far from the tissue edge (wound edge); a small size of the device such that it may be used for laparoscopic surgery, e.g. fitting a trocar; reliable placement of the device relative to the tissue to be sutured; user-friendliness to the surgeon; reliable operation when puncturing the tissue, e.g. little or no tearing; low risk for collateral damage to nearby tissue; etc.

SUMMARY

In view of the foregoing, herewith a suture device and method are provided as set out below.

An aspect comprises:

a suture device comprising an elongate body having a longitudinal axis and opposite proximal and distal ends with respect to the axis, the distal end being configured for insertion into a tissue wound and the proximal end being configured for operating the device, in particular for manual manipulation by a person's hand;

a suture needle connected with the elongate body at or near the distal end and movable relative to the elongate body in longitudinal direction along a needle trajectory having a suturing space;

a spreader being connected with the elongate body at or near the distal end and being configured to engage tissue to be sutured adjacent the needle trajectory and to provide a pulling force on the tissue to pull a portion of the tissue into the suturing space.

The suturing space is the part of the needle trajectory where the needle is to penetrate the tissue to be sutured; at least part of the suturing space may be defined by objects along which or through which the needle passes along the needle trajectory, e.g. a portion of the elongate body. By pulling the tissue into the suturing space, correct placement of the suture in the tissue may be ascertained; correct placement may comprise that the suture is placed sufficient distance from the tissue edge. Employing a pulling force reduces a risk of squeezing tissue out of a clamp and it may facilitate placing a suture, e.g. since the tissue may be stretched to some extent, thickness of the tissue may be reduced and/or folds in the tissue may be prevented. The needle trajectory may be determined by the shape of the needle, e.g., at least part of the trajectory being a continuation of the needle shape. In particular, the needle trajectory may be straight for a straight needle and it may be curved, e.g. (semi-) circular for an accordingly curved needle. In particular a straight needle trajectory may be entirely parallel to the longitudinal axis. Combinations of straight and curved needle trajectories and/or other options may be suitably employed.

The spreader may be configured to engage the tissue on opposite sides of the needle trajectory and to provide a pulling force on the tissue in a direction perpendicular to the needle trajectory and in particular perpendicular to the longitudinal axis. This provides one or more of spreading and/or pulling the tissue into the suturing space, prevention of unilateral forces on the tissue, and prevention of pulling forces on tissue outside the spreader.

The spreader may be configured to engage opposite sides of a tissue wound and to urge these opposite sides away from each other. Thus, the tissue wound is spread in one direction by the spreader and a pulling force is provided on the tissue urging the tissue wound sides towards each other and into the suturing space, e.g. forming a generally circular wound into an elongated ellipsoidal shape.

A portion of the spreader may be controllably outward movable relative to the longitudinal axis from a first, relatively narrow configuration, to a second relatively wide configuration for engaging and urging the tissue. Thus, the device may be positioned in the first configuration after which the spreader may be employed, so that interference of the spreader with the positioning may be prevented.

In particular, at least a portion of the spreader may be deformable, e.g. bendable and/or having a hinge that may be a living hinge, and the movable portion, e.g. a deformable portion, of the spreader may be resiliently movable. A deformable spreader may facilitate construction and reduce volume of the device. A resiliency may facilitate return of the spreader to the first configuration, which may ease operation and/or withdrawal of the device after operation.

The spreader may be attached to the elongate body on one side and the suture device may be provided with a spreader operator movable with respect to the elongate body for moving and/or deforming at least a portion of the spreader with respect to the elongate body. This facilitates operation of the spreader at a desired position and/or time. The spreader operator may be operable (e.g. movable or caused to move) from the proximal side of the device, e.g. in the form of a gripper with a trigger or a compressible grip or the like. In an example, the spreader is attached to the elongate body on one side and attached on an opposite side to a spreader operator on an opposite side wherein the spreader operator is movable with respect to the elongate body in longitudinal direction from a first separation from the elongate body to a second separation from the elongate body less than the first separation, such that in the second separation at least a portion of the spreader is moved, in particular being deformed, such as being bent.

Some embodiments may have a single needle or more than two needles. In the latter case, at least some the needles may be arranged as pairs of needles pairwise connected with suture thread and/or pairs of needles of which the needles forming a pair are arranged mutually opposite each other with respect to a plane comprising the longitudinal axis, which may facilitate providing plural sutures in one operation, in particular when the needles are held by the same needle holder. The needles of such pairs of needles may be arranged at equal or different distance to the plane and/or to other needles, e.g. providing pairs of equal widths and/or equal relative positions.

In an aspect, a suture device is provided, which may comprise any features of other aspects in any suitable combination, and which comprises an elongate body having a longitudinal axis and opposite proximal and distal ends, with respect to the axis, the distal end being configured for insertion into a tissue wound and the proximal end being configured for operating the device, in particular for manual manipulation by a person's hand;

a suture needle connected with the elongate body at or near the distal end and movable relative to the elongate body in longitudinal direction along a needle trajectory passing a suturing space;

wherein the suture device comprises a driver, in particular a spring, and the device is configured to urge at least a portion of the suture needle from a first position to a second position along a needle trajectory past a suturing space by a driving action of the driver, e.g. a spring action of the spring.

Thus, operation of the needle and penetrating the tissue to be sutured to make the suture may be assisted and possibly at least partly automated by the driving action, e.g. the spring action. Further, the needle may be moved more rapidly from the first position to the second position than when manually operated. Also, changes in position and/or force of (the suturing space) of the device resulting from manual operation of the device may be obviated. This may facilitate surgery and operation by the surgeon, including improving accurate placement of a suture. At least part of the driver may be arranged at or near the proximal end of the device, e.g. in a grip portion.

The driver may be at least partly powered e.g. comprising an electric, hydraulic and/or pneumatic driver, and/or be at least partly reversible and/or energy-conserving such as a spring.

In particular, a pneumatic driver may comprise a reservoir for holding a gas under pressure and/or a gas forming agent from which reservoir doses of a gas may be released in a controlled fashion to provide the driving action. The gas may be air, nitrogen, carbon dioxide, nitrous oxide, etc. The driver may comprise a connector for operating the driver and/or for charging the reservoir from an external gas pressure source.

An electric driver may provide an electromechanic driving action, e.g. a motor driving gears and/or a spindle etc. also or alternatively, an electric driver may provide an electromagnetic driving action, e.g. comprising a solenoid actuator for displacing a magnetic or magnetisable object. The electric driver may comprise a power source, e.g. a battery, and/or a connector to an external power supply, which may be a mains socket.

In a device comprising a spring, the spring may comprise or be at least one of: a mechanical spring, such as a resiliently deformable object and/or a coil spring and/or a leaf spring etc.; a gas-spring comprising a sealed reservoir for the gas, such as a sealed cylinder-piston assembly and/or a bellows etc.; and a magnetic spring, such as permanent magnets arranged with equal poles facing each other.

The suture device may comprise at least two suture needles connected with the elongate body at or near the distal end and movable relative to the elongate body in longitudinal direction along respective needle trajectories having respective suturing spaces on opposite sides of the elongate body, in particular diametrically opposite each other relative to the longitudinal axis. The needle trajectories may be entirely on opposite sides of the elongate body, in particular diametrically opposite each other relative to the longitudinal axis. This facilitates suturing tissue on opposite sides of the wound and facilitates closing the wound. It also obviates having to manoeuvre and reposition the device between positioning suture needles for different sutures/suture locations. Simultaneous movement and/or operation of the needles may be preferred, for which the needles may be held by two coupled needle holders or be held by a single needle holder.

In such case of at least two suture needles having respective suturing spaces on opposite sides of the elongate body, the spreader may be arranged to provide a pulling force on the tissue in a direction perpendicular to both needle trajectories. E.g., the spreader may be arranged perpendicular to a line through both suture spaces and/or a plane comprising both suture spaces. Thus, upon employment of the spreader, the tissue will "automatically" be pulled into the opposite suturing spaces by stretching of the tissue. A perpendicular arrangement may facilitate a compact construction of the device.

The spreader may be formed to provide equal pulling forces to and/or equal tissue displacement on opposite sides of a needle trajectory, possibly to opposite sides of two needle trajectories of plural needles. The spreader may be symmetric with respect to at least one of the longitudinal axis, the needle trajectory of one needle and the needle trajectories of plural needles, e.g. two needles on opposite sides of the device. Such devices may assist in lateral placement of a suture, in particular in placing a suture substantially in the middle of the wound.

The spreader may have a general V-shape facilitating spreading of the tissue by spreading action of the spreader at a relatively narrow portion of the V-shape and enabling to exert an additional pulling force on the tissue by maneuvering another, relatively wider part of the V-shape into the tissue.

The device, in particular the spreader, may have a lifting portion, e.g. one or more of a recess, a protrusion and/or a hook in a radial direction with respect to the longitudinal axis, for engaging the tissue and exerting a pulling force on the tissue in a proximal direction and/or exerting a pushing force on the tissue in a distal direction. Thus, the tissue to be sutured may be pulled towards and/or pushed away from the operator (e.g. a surgeon), in particular during application of a suture (e.g. penetration of the tissue), by which interference of/with adjacent tissue may be prevented. E.g., the wound sides to be sutured may be pulled clear from underlying tissue or from overlying tissue layers.

The spreader, in particular a spreader of a device according to the previous paragraph, may be used to orient the device during surgery, e.g. by providing rotational/torsion feedback to the surgeon inserting the device in the wound. A visual marker and/or a tactile marker may be provided on or near the proximal side of the device to assist orienting the device.

In case of an elongated or generally slit-like wound shape the device may preferably be oriented such that the spreader and its operational direction of engagement are along a major length of the wound and one or more needles are arranged along a minor length of the wound that may be perpendicular to the major length, to provide a suture along the minor length in accordance with a direction of most probable successful wound healing and/or of least tension on the suture and/or on the healing tissue.

In particular in laparoscopic surgery, a trocar puncture may have a generally circular shape or rather a slit-like shape. The spreader may be used to engage opposite sides of the wound and to urge these opposite sides away from each other and by that to bring the other tissue wound sides, in particular portions generally perpendicular to the sides that are engaged by the spreader, towards each other and into the suturing space. The suture thread may then be used to urge these latter sides of the wound together so as to facilitate healing of the wound by growing together of the sutured sides.

The suture device may comprise a needle holder connected at or near the distal end, in particular at or near the distal end of the operating element, to hold one or more suture needles, preferably such that a tip (the tips) of the one or more needles is (are) directed in proximal direction of the suture device. The suture device may comprise a shroud connected with the elongate body at or near the distal end, wherein the needle, and/or the needle holder when present, is at least partially movably with respect to the shroud between at least a protecting position wherein at least the tip(s) of the needle(s) is (are) shielded by the shroud, and a non-protecting position wherein the tip(s) is (are) unshielded by the shroud and the needle(s) is (are) movable relative to the elongate body along the needle trajectory through the suturing space. The shroud may be movable relative to the elongate body. The shroud may be spaced from the elongate body in the longitudinal direction to provide the suturing space in between.

The needle holder facilitates movement of the needle with respect to the elongate body and here also with respect to shroud and the needle holder may be configured to hold the needle releasably, e.g. such that the needle may be transferred from the needle holder to a needle receptacle, enabling transfer of the needle through the tissue in a one-way operation.

The shroud facilitates use of the device in the body with reduced or prevented risk of damaging tissue by an exposed needle tip. The needle holder may be connected at a distal end of an operating element connected to the elongate body, possibly contained in the elongate body. The operating element may be movable with respect to the elongate body and/or the shroud.

Part of the shroud may be configured for manipulating tissue, e.g. for urging the tissue to be sutured in a desired direction such as pulling tissue up or pushing tissue away.

The shroud may be movable with respect to the elongate body, in particular for moving and/or deforming at least a portion of the spreader with respect to the elongate body. The spreader may be attached to the shroud. The shroud may be operable from the proximal side of the device and it may be movable with respect to the elongate body in longitudinal direction from a first to a second separation from the elongate body and be operative as a spreader operator as set out above. Thus, a simple construction of the device may be possible.

The suture device may comprise a driving portion, in particular a resilient element, and the device may then be configured to cause the spreader to engage the tissue and to pull a portion of the tissue into the suturing space by a driving action of the driving portion, e.g. by spring action of the resilient element. This may facilitate construction and/or operation of the device, obviating active operation and/or actuation of the spreader. The driving portion may be the aforementioned driver; in particular, the optional resilient element may be the aforementioned spring. Where a movable shroud is present, (the driving action of) the driving portion, e.g. (the spring action of) the resilient element, may operably act on the shroud such that the latter may act as a spreader operator.

The suture device may comprise a relatively narrow waist and the suturing space may be located in the waist. In particular the waist may be provided between the elongate body and the shroud, when present. The spreader may be operably located at the position of the waist, seen with respect to the longitudinal axis.

Such waist may facilitate (ascertaining) correct longitudinal placement of the device relative to the tissue to be sutured. The waist may be symmetric with respect to the longitudinal axis. Further, the needle(s) can pass between the shroud and the elongate body through the waist and any tissue received therein, in particular along a straight trajectory that may be parallel to the longitudinal axis. Also, the waist facilitates accommodating a natural tendency of tissue to close a puncture wound with tissue edges near to each other. It further enables reduction of a device volume both for introducing and/or moving the device into and/or through a trocar and when manipulating the device within the tissue/body. The device may formed complementary to a trocar and/or provided with a trocar, e.g. as an assembly of a trocar and the device. In such cases, the trocar and/or the device may comprise one or more connectors for connecting the trocar and the device together in one or more predetermined configurations which may comprise one or more relative orientations. E.g., a predetermined configuration may comprise holding, e.g. (preferably releasably) fixing a relative orientation of the spreader to a trocar for aligning a spreading direction with a cutting direction of the trocar so that an operational spreading direction of the spreader corresponds with a longitudinal direction of a slit shaped wound made by the trocar. The trocar and/or the device may comprise at or near its/their proximal side an indicator for indicating an operational direction of the spreader (e.g. a spreading direction) and/or the trocar (e.g. a cutting direction). The aforementioned one or more connectors may enable adaptation of devices and/or trocars of different sizes and/or types to each other, e.g. one device fitting trocars of different designs by virtue of an appropriate connector or series of connectors. Thus connected, the device and trocar may be inserted and/or operated and/or withdrawn as a single assembly and/or with a single manipulation/manipulation sequence. This may reduce complexity and/or duration of a surgical procedure.

In case of a suture device comprising a spring and the device being configured to urge at least a portion of the suture needle by a spring action of the spring, the device may comprise a latch that is controllably movable between a first position and a second position and the device may be configured such that the spring is deformable to a first configuration in which the spring is tensioned compared to a relaxed state for the spring action and the spring can be maintained in the first configuration by the latch being in the first position, and such that by movement of the latch from the first to position to the second position the spring can be released for providing the spring action, at least partly relaxing to a second configuration. Thus, the spring may be pre-tensioned and by movement of the latch the spring can be released and activated so as to (cause to) operatively move the suture needle(s) to penetrate the tissue to be sutured. In such embodiment, The latch may be controllably movable at or near the proximal end of the elongate body, facilitating use. Also, the spring may be located at or near the proximal end of the device, where sufficient space may be available and by which a weight balance of the device may be improved. The latch may be operable by movement of a latch operating element in perpendicular direction to the longitudinal axis, or in another direction that may prevent longitudinal forces and/or movement of the device and/or that may be ergonomically convenient to an operator (e.g. a surgeon).

If the device comprises a movable and/or deformable spreader and a spring configured for at least partly activating the spreader, the device may be configured such that the spring is deformable to a third configuration in which the spring is further tensioned than in the first configuration, and wherein the device is configured to couple the spreader with the spring and cause the spreader to engage the tissue and to pull a portion of the tissue into the suturing space by a spring action of the spring relaxing from the third configuration to the first configuration, after which the spring can further relax to the second configuration for at least partly assisting operation the suture needles as discussed above. Thus, the spring may serve for deploying the spreader and then (still) be "armed" in the first configuration for urging the needles as discussed above. Alternatively, different springs can be used for different functions and/or operating different portions of the device.

If the device comprises a spring for urging at least a portion of the suture needle from a first position to a second position along a needle trajectory past a suturing space, and/or for at least partly activating the spreader, the device may be configured such that, in the device, the spring is arrangeable in a fourth configuration in which the spring is substantially relaxed, compared to other use configurations, possibly being fully relaxed, and the spring is deformable to at least one of the first configuration and the third configuration, in which the spring is at least partly tensioned compared to the fourth configuration. This reduces or prevents permanent loading of the spring and/or device portions, e.g. extending shelf life of the device, and/or serving as a signal of first-time use.

In the foregoing, the spring may be formed and/or be replaced at least in part by a deformable gas-pressurisable or gas-pressurised reservoir, e.g. a cylinder-piston combination and/or a bellows.

Any of the described device embodiments may be modular, in particular comprising a first module and a second module, connectable together for assembling (an according embodiment of) the device. The first module may comprise the spreader, and optionally one or more of: a needle holder, one or more suture needles, suture thread and a shroud, in any combination and/or form as described herein. The second module may comprise the elongate body and one or more of a latch, a button, a spring, a release button, and a connector, in any combination and/or form as described herein. Either module may further comprise at least part of a shaft as described herein.

Another aspect comprises a method of suturing tissue. The method comprising providing a suturing device comprising an elongate body and a suture needle, the elongate body having a longitudinal axis and opposite proximal and distal ends, the distal end being configured for insertion into a tissue wound and the proximal end being configured for manual manipulation by a person's hand and the suture needle being connected with the elongate body at or near the distal end and movable relative to the elongate body in longitudinal direction along a needle trajectory passing a suturing space. The method comprises the step of engaging tissue to be sutured on opposite sides of the needle trajectory and pulling a portion of the tissue into the suturing space, in particular by pulling on the tissue in a direction perpendicular to the needle trajectory and more in particular perpendicular to the longitudinal axis; and the step of penetrating the tissue with the suture needle in the suturing space by moving the suture needle relative to the elongate body along the needle trajectory.

Thus, the tissue may be properly positioned for suturing in an efficient manner.

BRIEF DESCRIPTION OF THE DRAWINGS

The above-described aspects will hereafter be more explained with further details and benefits with reference to the drawings showing a number of embodiments by way of example.

FIG. 1 is an exploded view of a suture device;

FIG. 1A indicates a tissue wound to be sutured;

FIG. 2A shows the suture device in a first configuration, FIGS. 2B-2D are side, top and bottom views, respectively, of the device in the first configuration; FIGS. 2E, 2G, 2I, 2J, 2K and 2L are cross section views as indicated in FIGS. 2B-2D, FIGS. 2F and 2H are details of FIGS. 2E, 2G, respectively, as indicated in the latter Figs.;

FIGS. 3A-3K show, like FIGS. 2A-2K, the suture device in a second configuration;

FIGS. 4A-4K show, like FIGS. 2A-2K, the suture device in a third configuration; FIG. 4L is a cross section view like FIG. 2L in the third configuration;

FIGS. 5A-5L show, like FIGS. 2A-2L, the suture device in a fourth configuration; FIG. 5L is a cross section view like FIG. 2L in the fourth configuration;

FIGS. 6A-6L show, like FIGS. 2A-2L, the suture device in a fifth configuration; FIG. 6L is a cross section view like FIG. 2L in the fifth configuration; FIG. 6M is a cross section view like 6L at a later moment of use of the device;

FIG. 7 indicates the tissue wound after operation of the suture device.

NB: FIGS. 2L, 4L, 5L, 6L and 6M are shown adjacent each other on a separate sheet which also shows FIGS. 1A and 7;

FIGS. 8*ii*-8*vi*' and, respectively, FIG. 9 are cross section views and tissue wound views as in FIGS. 2L, 4L, 5L, 6L, 6M and, respectively, FIG. 7, of another embodiment providing plural sutures simultaneously.

DETAILED DESCRIPTION OF EMBODIMENTS

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral, where helpful individualised with alphabetic suffixes.

Further, unless otherwise specified, terms like "detachable" and "removably connected" mean that respective parts may be disconnected essentially without destruction of either part, e.g. excluding structures in which the parts are integral (such as welded or molded as one piece), but including structures in which parts are attached by or as mated connectors, fasteners, releasable self-fastening features, etc.

FIG. 1 shows an embodiment of a suture device 1 as provided herein in an exploded view. The device comprises an elongate body 3 having a longitudinal axis A and proximal and distal ends P, D, respectively, arranged along the axis A. The distal end D is configured for insertion into a tissue wound T (see FIG. 1A) and the proximal end P is configured for manual manipulation by a person's hand. FIG. 1A schematically indicates a piece of tissue T having a tissue wound TW to be sutured defined by a tissue edge TE. The shown wound TW has an elongated, substantially slit-shaped shape, so that the tissue edge TE may be generally divided into relatively long and close first and second opposite tissue edge portions TE1, TE2, and relatively short and far third and fourth opposite tissue edge portions TE3, TE4.

In the shown embodiment, the body 3 comprises a relatively narrow shaft section 5 and a relatively wide grip portion 7 at the proximal end P. At the proximal end P a push button 9, a spring 11 and a release button 13 are provided. The push bottom 9 is hollow, accommodating the spring 11 in its interior (FIGS. 1, 2E, 2G). In the interior a snap connector in the form of latching fingers 10 is provided (FIGS. 2E, 2G). The shown body 3 is tubular and the shaft 5 has optional openings saving weight and facilitating sterilisation.

A spreader 15, to be discussed in detail below, is connected with the elongate shaft 5 at the distal end D. The spreader 15 may be integral with portions of the body 3 or be provided as a separate element attached to the body 3, as shown, so that different materials may be used for the shaft 5 and the spreader 15. The attachment may be permanent or releasable. A shroud 17 is provided on a distal side of the spreader 15.

Further, the device 1 comprises a connector 19, an inner shaft 21, a needle holder 23 or "slider", and two suture needles 25 connected with suture thread 27. The inner shaft 21 may be at least partly tubular and accommodate at least part of the suture thread 27.

The connector 19 provides positional interlocks, here formed as portions 19A-19F of different size (here different diameter) providing stepped thickness transitions. The connector 19, and the inner shaft 21 are, in assembled state, see below, fixed together and connected to the needle holder 23 forming an operating element 29 to the latter as explained below.

The device 1 may be modular. E.g., a first module may be provided as a suture assembly module M1 and may comprise the spreader 15, needle holder 23, needles 25 and suture thread 27, optionally also a shroud 17; a second module may be provided as a body module M2 and may comprise the body 3 and its associated operating parts such as button 9, spring 11 and release button 13, and it may comprise the connector 19.

FIGS. 2A-2K show the device 1 in an assembled state and in a first configuration, e.g. suitable for storage of the device and for introducing the device 1 into a wound site with tissue to be sutured. The device 1 may be provided assembled as shown in FIG. 2A-2K, or as modules to be assembled prior to use into the configuration of FIGS. 2A-2K.

The device 1 may comprise one or more connectors for connection to a trocar (not shown) and/or an adaptor (not shown) for fitting the device 1 to a trocar. The device 1 may adjusted to fit a particular trocar, e.g. having a proprietary connector mated to a proprietary counterconnector of a particular (type of) trocar, and/or the device may be provided as an assembly with one or more adapters to different types and/or size trocars.

The needle holder 23 may be (optionally detachably) attachable to the inner shaft 21 and/or the inner shaft 21 may be (optionally detachably) attachable to the connector 19. Thus, the inner shaft 21 may be comprised in either module M1, M2, or, possibly, the inner shaft 21 may be provided as a separate shaft module. In an embodiment (not shown), the shaft 21 is a multi-part object, e.g. a two-part object, and either one of the suture assembly module M1 and the body module M2 may comprise an according shaft part.

In case the inner shaft 21 is comprised in the suture body module M1 and the inner shaft 21 is at least partly tubular, at least a portion of the suture thread 27 may be accommodated inside a tubular portion of the inner shaft 21 in the module. In other embodiments, also or alternatively, at least a portion of the suture thread 27 may be accommodated inside at least part of the slider 23 and/or the shroud. Either way thus stored, the suture thread 27 may be protected from one or more of snagging, knotting, damaging and/or contamination.

In (modules of) the device 1, releasable connections may be formed in various ways, e.g. by detachable latching (latches having release features such as pulling tabs), bayonet connection and/or screw threads; in the latter cases features such as noncircular portions, ribs, recesses, interlocks, etc may be provided to prevent relative rotation of parts, at least beyond a certain angle, and substantially only enable translational relative movement of the parts. Two or more of the modules may comprise mated connectors for assembly of the device 1 in a limited number of specific configurations, e.g. in relative orientations of two modules. A connector may be integrally formed with one or more other device portions such as the spreader 15 as shown. Different suture assembly modules M1 may comprise the same connection and/or be configured for use with one or more different needles, suture threads, spreaders etc. for use with the same body module M2.

Providing the device 1 as a modular device allows that different modules (in particular suture assembly module M1 and body assembly module M2) may be treated independently, e.g. according to different standards regarding one or more of manufacturing, sterilisation, packaging, certification, sale, storage, shelf life, use, (partial) reuse, disposal, etc.

Referring again to FIGS. 2A-2K, in the shown assembled state and first configuration, the grip portion 7 and the push button 9 are inserted into each other. Here, they are both hollow and together house the spring 11. The grip portion 7 and the push button 9 are movably attached together, here by interlocking elements in the form of resilient latches 31 and windows 33. In this configuration the spring 11 may be in a fully relaxed state or slightly tensioned by compression, urging the push button 9 outward from the grip portion 7 (urging the button 9 in proximal direction). The push button may be asymmetric, as shown, having an extending finger 34 on one side (see FIGS. 2E-2G). In another embodiment, at least part of the handle 7 may be formed as, or provided with, a deformable pneumatic reservoir as a spring, instead of comprising the shown coil spring 11, in which case the reservoir may be sealed and/or provided with a connection to an external gas pressure source. Also or alternatively, the handle 7 may comprise a solenoid and the connector 19 and/or shaft 21 may be provided with, or be at least partly replaced by, a magnetic or magnetizable material, in which case the device may comprise a battery and/or be provided with a connection to an external electric power source.

The body 3 and the shroud 17 are at least partially hollow, e.g. tubular, housing the operating element 29 and the needle holder 23. The release button 13 in the shown embodiment comprises, here defined at least partly by a rim 35 and walls 37, an opening 38 through which the operating element 29 extends. The release button 13 is slidably arranged in the grip portion 7 and it is spring biased outward relative to the axial direction. The spring bias is due to a spring portion 39, which is unitarily included in the release button 13, but which may be a separate part. The spring portion engages a stop 41 of the body 3, the rim 35 engaging the connector 19. The release button 13 further comprises a second opening 42.

In the first configuration, the rim 35 abuts a narrow portion 19D of the connector 19, preventing the operating element 29 from moving in proximal direction relative to the body 3 (FIGS. 1, 2E, 2I). At the same time, the flange portion 19C of the connector 19 abuts the walls 37 (FIGS. 2E, 2J) preventing the operating element 29 from moving in distal direction relative to the body 3. Thus, the operating element 29 is fixed in position relative to the body 3.

The needle holder 23 is fixed to the inner shaft 21 of the operating element 29. The distal ends 25A of the needles 25 are held by the needle holder 23, the proximal ends 25B of the needles 25 form tips for penetrating tissue. As visible in FIGS. 2G, 2H, the needle holder 23 and the inner shaft 21 may be at least partly tubular and accommodate at least part of the suture thread 27.

In the first configuration, the needle holder 23, fixed to the inner shaft 21, is clamped, or friction-fit, in position in the shroud 17 with tongues 43 engaging (an inner wall of) the shroud 17 (FIGS. 2C-2F, 2K). In this position the needle holder 23 and the shroud 17 are in a relative protecting position wherein at least the tips of the needles 25 held by the needle holder 23 are shielded by the shroud 17 preventing tissue harm.

The spreader 15 comprises two arms 45 on opposite sides of the longitudinal axis A, here on diametrically opposite sides. The arms 45 extend between the body 3 and the shroud 17. The arms 45 are attached to the body 3 on their proximal side, here being hingedly attached to an optional connecting portion 47 of the spreader 15. Here, the arms 45 and the connecting portion 47 are formed as an integral part, the hinges being living hinges 49. The arms 45 movably engage the shroud on their distal side. The shown arms 45 are elastically deformable as a two-part structure with proximal arm portions 45A and distal arm portions 45B, in particular being bendable at a living hinge 51.

At the distal end of the elongate body, here being included in the connection portion 47, needle traps 52 are provided, see below.

Best seen in FIGS. 2G-2H, between the body 3 and the shroud 17 the device 1 has a narrow waist W providing recesses in the general outline of the device 1 resulting from the shapes of the body 3 and the shroud 17. The recesses define part of the suturing space S of each needle 25 and accommodate the tissue to be sutured (not shown). Needle trajectories N run through the suturing spaces S. Here, the waist W is formed by an extension part of the shroud 17 which movably fits in an opening at the distal end of the elongate body 3 and/or, as shown here, in the optional connection portion 47 of the spreader 15. The waist may have a non-circular cross sectional shape as shown. The axial position of the spreader 15 coincides with that of the waist W.

In use, and as shown in FIG. 2L, the distal end D of the device 1 is inserted into the tissue wound TW with the device 1 being in the first configuration, and the device 1 is manipulated such that the tissue edges TE of the tissue to be sutured are located adjacent the waist W of the device 1, and possibly at least partly received in the waist (not shown). For the insertion, the device 1 may be fed through a trocar previously inserted into the tissue wound TW (possibly being the trocar with which the tissue wound TW was made), or the device 1 and the trocar (not shown) may be coupled and inserted together.

Due to narrowing of the waist W and the non-circular cross section formed by the waist W and the spreader 15, contact of the waist W and/or spreader 15, with the tissue edge TE and/or tension in the tissue to be sutured may provide feedback on the axial and/or rotational position of (the waist W of) the device 1 in the wound (not shown).

When the device 1 is correctly positioned, the user (surgeon) depresses the button 9 fully into the grip portion 7 in distal direction, thus compressing and tensioning the spring 11, to transform the suture device 1 in a second configuration, as shown in FIGS. 3A-3K. In this configuration, the latching fingers 10 snap onto a proximal disk 19A of the connector 19 so that the button 9 and the operating element 29 become fixed to each other (FIGS. 3E, 3G). This second configuration may also be called the connected configuration.

Further, the push button 13 may be pushed radially aside so that the rim 35 frees the narrow portion 19D of the connector 19 and the opening 38 is ready to accept a wider portion 19E of the connector 19 (FIGS. 1, 3E, 3I) in a subsequent configuration (see below). Here the pushing-aside of the push button 13 is automatically done by the extending finger 34 of the button 9 which extends into the window 42 of the push button 13 (FIGS. 2G, 2I, 2J); compare FIGS. 2A-2D, 2G, 2I-2J with FIGS. 3A-3D, 3G, 3I-3J. For this automated action, the finger 34 and/or the window 42 may be at least partly bevelled as shown.

In the first and second configurations, the distal portion of the device is unchanged. A schematic cross section Figure at position L would be the same as that of the first configuration, see FIG. 2L.

Next, the push button 9 is released and by spring action of the spring 11 the suture device 1 is transformed into a third configuration, shown in FIGS. 4A-4K. By this, the spring 11 is partially relaxed urging the button 9 some distance in proximal direction from the grip portion 7 (compare FIGS. 3A, 3B, 3G with FIGS. 4A, 4B, 4G). Due to the (snap) connection between (the latching fingers 10 of) the button 9 and the connector 19, this causes that the connector 19 and the operating element 29 as a whole are pulled in proximal direction, until the wider portion 19E of the connector 19 engages the rim 35 of the push button 13 (FIGS. 1, 4E, 4I) halting further motion in proximal direction. By this movement of the operating element 29, the needle holder 23 and the shroud 17 are also moved in proximal direction relative to the elongate body 3. In this embodiment the movement of the shroud 17 is due to the clamping force between the needle holder 23 and the shroud 17, and the movement is limited by an edge 53 on the waist W abutting a distal portion of the connecting portion 47 or, as the case may be, of the elongate body 3 (e.g. compare FIGS. 3F and 4F). In this third configuration the needle holder 23 and the shroud 17 are still in the relative protecting position wherein at least the tips of the needles 25 held by the needle holder 23 are shielded by the shroud 17. Best seen in FIG. 4D is that in this embodiment the arms 45 of the spreader 15 and a line of shortest distance between the needles 25 extend in mutually perpendicular directions, the arrangement here being centered about the longitudinal axis A. In other words, in the present embodiment the spreader 15 is arranged to spread the tissue substantially in a direction normal to a plane comprising both parallel needles 25.

By the movement of the shroud 17 with respect to the elongate body 3, and thus due to the spring action of the spring 11, the spreader 15 is deformed from a relatively narrow configuration to a relatively wide configuration, wherein the arms 45 are bent at the hinges 49, 51; compare FIGS. 2A, 2B, 2D-2F/3A, 3B, 3D-3F with FIGS. 4A, 4B, 4D-4F, and FIG. 2L with FIG. 4L. In this position, best seen in FIG. 4L, the tissue to be sutured is engaged, at tissue edge portions TE3, TE4, and urged outward by (the legs 45 of) the spreader 15, in particular at the position of the hinges 51, in a direction perpendicular to the needle trajectory T and in particular perpendicular to the longitudinal axis A. This spreads the wound TW to be sutured in one direction (the widest direction) and in a perpendicular direction pulls opposite sides TE1, TE2, of the wound tissue to be sutured into the suturing space S. In the shown embodiment the spreader 15 is symmetric with respect to the longitudinal axis A and therefore the positions of the needles 25 will be substantially in the middle of the (stretched) wound TW (see also below). However, the device may be asymmetric (not shown).

Note that instead of by spring action, the spreader 15 could be deployed (spread from a narrow to a wide configuration) by manual operation by movement of the operating element 29 relative to the elongate body 3 if a suitable handle were attached to the operating element 29 instead of the knob 9 as shown.

One or both sides of the spreader 15, may comprise a recess for accommodating a portion of (an edge of) the tissue, e.g. a recess towards the axis A at the position of the hinge 51, which may assist in one or more of engaging the tissue, aligning the device and the tissue with respect to each other in axial direction, and maintaining a position of the device and the tissue with respect to each other in axial direction. Also, or alternatively, one or both arm portions 45A, 45B, in particular the distal arm portion 45B on one or both sides of the spreader 15, may comprise a hook portion (see protrusion 53 in radial outward schematically indicated in FIG. 4F) for further manipulating the tissue to be sutured, in particular in axial direction, e.g. lifting the tissue.

Next, the release button 13 is pushed in and by spring action of the spring 11 the suture device 1 is transformed into a fourth configuration, shown in FIGS. 5A-5L. FIGS. 4A-4K and 5A-5K actually show another embodiment of the device 1' wherein the arms 45 of the spreader 15' are integrally formed to the elongate body 3', so that a connection portion 47 is absent. Otherwise the devices 1, 1' are the same.

For this fourth configuration, the push button 13 is pushed radially aside further inwards so that the rim 35 frees the wider portion 19E of the connector 19 and the opening 38 is ready to accept the still wider and distal portion 19F of the connector 19, see FIG. 1 and compare Figs. FIGS. 4A-4D, 4G, 4I-4J with FIGS. 5A-5D, 5G, 5I-5J. Thereby, the spring 11 is further relaxed urging the button 9 in proximal direction from the grip portion 7 (compare FIGS. 4A, 4B, 4G with FIGS. 5A, 5B, 5G). Due to the snap connection between (the latching fingers 10 of) the button 9 and the connector 19, this causes that the needle holder 23 is pulled in proximal direction and slides through the shroud 17 so that the needles 25 are moved relative to the elongate body 3' in longitudinal direction along their respective needle trajectories N at least partly out of the shroud 17 and through the suturing spaces S, piercing any tissue T accommodated in the latter (compare FIGS. 4A, 4B, 4G, 4H, 4L with FIGS. 5A, 5B, 5G, 5H, 5L).

Further, by the movement the proximal ends 25B of the suture needles 25 are caught and fixed in the respective needle traps 55. Thus, by actuating the push button 13 on the proximal end P the tissue T is penetrated by the suturing needles 25 (FIG. 5L). The spring constant of the spring 11 determines the force with which the tissue T can be penetrated, subject to any friction in the device 1.

Note that in the shown device 1, 1' the friction force and any attachment force of the needle holder 23 relative to the shroud 17 must, in sum, be higher than the total of the forces required for moving the shroud 17 relative to the elongate body 3 and for deforming the spreader 15. Further, the pulling force of the spring 11 on the needle holder 23 after actuation of the release button 13 and blocking movement of the shroud in proximal direction must be higher than the friction force and any attachment force of the needle holder 23 relative to the shroud 17.

Next, the user (surgeon) depresses again the button 9 into the grip portion 7 in distal direction, thus compressing and tensioning the spring 11, to transform the suture device 1 in a fifth configuration, as shown in FIGS. 6A-6L. In this configuration, due to the fixation of the proximal ends 25B of the needles 25 in the needle traps 52 the needle holder 23 is pushed off the distal ends 25A, separating them. Further, the shroud 17 and the needle holder 23 are moved in distal direction with respect to the elongate body 23 by which the needles 25 are freed from the shroud 17 and the spreader 15 is relaxed back toward a narrow configuration; see FIG. 6L.

The suture thread 27 being fixed to the distal ends 25A of the suturing needles 25 is freed from the inner shaft 21 of the operating element 29 and after the distal ends 25A are pulled fully through the tissue T, the suture thread 27 is pulled through; see FIG. 6M.

The suturing device 1 can then be pulled in proximate direction from the wound TW, by which the suturing thread 27 is pulled through the tissue and out of the inner shaft 21 and the shroud 17, so that after removal of the device from the tissue only the suturing thread 27 remains, laced through the tissue T on opposite sides of the tissue wound TW, see FIG. 7. In case the suturing device 1 is connected with a trocar (not shown), the assembly of device 1 and trocar may be withdrawn together. The thread 27 can then be tensioned and suitably fastened such as by one or more of by tying, clamping, gluing, welding, etc., to bring the opposite tissue edges TE1, TE2 together for tissue healing. After fastening the thread 27, possible excess thread material may be cut and removed to finish the suture (not shown).

The device can thereafter be discarded, although in some embodiments the device can at least partly be reused.

In particular for large wounds, provision of plural sutures may be desired. For this, a device comprising plural pairs of needles may be used, as indicated in FIGS. 8ii-8vi' and 9 showing cross section views and tissue wound views as in FIGS. 2L, 4L, 5L, 6L, 6M and 7, discussed above. Thus, plural sutures (her: two, but more may be possible) may be provided in one operation and simultaneously. Such device may be shaped larger, smaller or of equal size to that of the previously discussed embodiments. When using plural sutures and/or simultaneous application of plural sutures this may provide one or more of, each suture subjecting lower local forces to the tissue, protecting the tissue, protecting the suture thread, enabling placing a suture closer to a tissue edge, enabling placing sutures closer to each other, facilitating and/or speeding up surgery, reduction of waste (discarded devices/device parts). Also or alternatively, several devices with or without spreader may be used in succession.

Also or alternatively the device may be "reloaded" with new needles and suture thread and/or with a new suture assembly module M1. In a modular embodiment one module may be reused whereas the other module may be discarded. In case of a modular device, e.g. see FIG. 1, different suture assemblies M1 may be used, which may comprise different sizes, numbers and/or arrangements of needles. A reloaded and/or reassembled device may be coupled with a trocar used in the preceding suturing operation or with another trocar.

Note that the spreader need not be symmetric but may be asymmetric, e.g. having different lengths and/or having one set of arms with two hinges instead of one. An asymmetric spreader may assist positioning (the longitudinal axis of) the device at a desired position, e.g. a position offset from a centre of a wound. Using plural such asymmetric devices with different offsets and/or offsets to different directions relative to the longitudinal direction of the wound facilitates placing a series of sutures at particular mutual separation, e.g. with a predetermined separation along a longitudinal direction of a wound (cf. FIG. 9).

Note that in the shown device 1, 1', for removal of the device from the wound and leaving the tread 27 in and suitably unwinding the thread, the sum of the friction force and any attachment force which hold the needles 25 in the needle traps 52, should be higher than the total of the friction force and any attachment force of the needle holder 23 relative to the shroud 17 plus the total of the forces required for moving the shroud 17 away from to the elongate body 3 (which may be reduced by relaxation forces of the spreader 15) plus the total of the friction force and any attachment force of the needles 25 to the needle holder 23.

Also, the pulling force of the spring 11 on the needle holder 23 after actuation of the release button 13 and blocking movement of the shroud 17 in proximal direction should be higher than the friction force and any attachment force of the needle holder 23 relative to the shroud 17.

However, in other embodiments latches may be provided to ensure relative positions of different portions of the device involved.

The disclosure is not restricted to the above described embodiments which can be varied in a number of ways within the scope of the claims. For instance the spreader may take the form of one or more rotary arms that may be rotary an axis parallel to the longitudinal axis A. Also, the push button 9 and the release button 13 are just examples of operating elements (their operation to be discussed below) that could be shaped and positioned different, e.g. as handles, pull triggers, sliders, etc. and any combination thereof.

Elements and aspects discussed for or in relation with a particular embodiment may be suitably combined with elements and aspects of other embodiments, unless explicitly stated otherwise.

The invention claimed is:

1. A suture device comprising:
   an elongate body having a longitudinal axis and opposite proximal and distal ends, the distal end being configured for insertion into a tissue wound and the proximal end being configured for operating the device;
   a suture needle connected with the elongate body at or near the distal end and movable relative to the elongate body in a longitudinal direction along a needle trajectory having a suturing space; and
   a spreader connected with the elongate body at or near the distal end and configured to engage tissue to be sutured adjacent the needle trajectory and configured to engage opposite sides of the tissue wound and to urge these opposite sides away from each other to provide a pulling force on the tissue to pull a portion of the tissue into the suturing space.

2. The suture device according to claim 1,
   wherein the spreader is configured to engage the tissue on opposite sides of the needle trajectory and to provide a pulling force on the tissue in a direction perpendicular to the needle trajectory.

3. The suture device of claim 2 wherein the spreader is configured to provide the pulling force on the tissue perpendicular to the longitudinal axis.

4. The suture device according to claim 1,
   wherein at least a portion of the spreader is controllably outward movable relative to the longitudinal axis from a first configuration that is relatively narrow to a second, configuration that is relatively wide for engaging and urging the opposite sides of the tissue away from each other.

5. The suture device according to claim 4, comprising
   a spring and wherein the device is configured such that the spring is deformable to a third configuration in which the spring is further tensioned than in the first configuration, and
   wherein the device is configured to couple the spreader with the spring and cause the spreader to engage the tissue and to pull a portion of the tissue into the suturing space by a spring action of the spring relaxing from the third configuration to the second configuration.

6. The suture device of claim 4 wherein at least a portion of the spreader is deformable.

7. The suture device of claim 4 wherein the movable portion of the spreader is resiliently movable.

8. The suture device according to claim 1, comprising a driver configured to urge at least a portion of the suture needle from a first position to a second position along a needle trajectory past a suturing space.

9. The suture device according to claim 8, comprising:
   a latch controllably movable between a first position and a second position; and
   wherein the driver is a spring, the spring being deformable to a first configuration in which spring actio of the spring is tensioned compared to a relaxed state for the spring action and the spring is maintained in the first configuration by the latch being in the first position, and such that by movement of the latch from the first position to the second position the spring relaxes at least partly to a second configuration.

10. The device according to claim 8,
   wherein at least a portion of the spreader is controllably outward movable relative to the longitudinal axis from a first configuration that is relatively narrow to a second, configuration that is relatively wide for engaging and urging the opposite sides of the tissue away from each other, and
   wherein the device is configured such that, in the device, the driver is arrangeable in a fourth configuration in which the spring is substantially relaxed compared to other use configurations and the spring is deformable to at least one of the first configuration in which the spring is at least partly tensioned compared to the fourth configuration.

11. The suture device according to claim 1,
   comprising at least two suture needles connected with the elongate body at or near the distal end and movable relative to the elongate body in longitudinal direction along respective needle trajectories having respective suturing spaces on opposite sides of the elongate body.

12. The suture device according to claim 1, wherein the spreader is arranged to provide a pulling force on the tissue in a direction perpendicular to both needle trajectories.

13. The suture device of claim 12 wherein the spreader is arranged perpendicular to a line through both suture spaces or a plane comprising both suture spaces.

14. The suture device according to claim 1, comprising a needle holder connected at or near the distal end to hold one or more suture needles each having a tip;

a shroud connected with the elongate body at or near the distal end, and movable relative to the elongate body, wherein the needle holder is at least partially movable with respect to the shroud between at least a protecting position wherein at least one or more tips of the one or more suture needles held by the needle holder are shielded by the shroud, and a non-protecting position wherein the one or more tips are unshielded by the shroud and the one or more suture needles are movable relative to the elongate body along the needle trajectory through the suturing space, and wherein the shroud is spaced from the elongate body in the longitudinal direction to provide the suturing space between the shroud and the elongate body.

15. The suture device according to claim 14, wherein the shroud is movable with respect to the elongate body for moving and/or deforming at least a portion of the spreader with respect to the elongate body.

16. The suture device according to claim 14, comprising a driving portion configured to cause the spreader to engage the tissue and to pull a portion of the tissue into the suturing space, the driving portion acting on the shroud.

17. The suture device of claim 14 wherein the needle holder is connected at or near the distal end to hold the one or more suture needles such that a tip of each of the one or more suture needles is directed in proximal direction of the suture device.

18. The suture device according to claim 1, wherein the suture device comprises a relatively narrow waist and the suturing space is located in the waist.

19. A method of suturing tissue, comprising providing a suturing device comprising an elongate body and a suture needle, the elongate body having a longitudinal axis and opposite proximal and distal ends, the distal end being configured for insertion into a tissue wound and the proximal end being configured for manual manipulation by a person's hand and the suture needle being connected with the elongate body at or near the distal end and movable relative to the elongate body in longitudinal direction along a needle trajectory passing a suturing space;

engaging tissue to be sutured on opposite sides of the needle trajectory and pulling a portion of the tissue into the suturing space, in a direction perpendicular to the needle trajectory by engaging other sides of the tissue wound and using these other sides away from each other; and penetrating the portion of the tissue in the suturing space with the suture needle by moving the suture needle relative to the elongate body along the needle trajectory.

* * * * *